United States Patent
Lee et al.

(10) Patent No.: US 9,872,097 B2
(45) Date of Patent: Jan. 16, 2018

(54) OPTICAL HEART RATE EARPHONE

(71) Applicant: Cheng Uei Precision Industry Co., Ltd., New Taipei (TW)

(72) Inventors: James Lee, New Taipei (TW); Kuo Yang Wu, New Taipei (TW); Wen Bing Hsu, New Taipei (TW); Hsiang Ling Chung, New Taipei (TW); Ching Jang Shyr, New Taipei (TW); Tsung Hsun Yu, New Taipei (TW); Hsiu Fen Wang, New Taipei (TW)

(73) Assignee: Cheng Uei Precision Industry Co., Ltd., New Taipei (TW)

( * ) Notice: Subject to any disclaimer, the term of this patent is extended or adjusted under 35 U.S.C. 154(b) by 3 days.

(21) Appl. No.: 15/246,640

(22) Filed: Aug. 25, 2016

(65) Prior Publication Data
US 2017/0339480 A1 Nov. 23, 2017

(30) Foreign Application Priority Data
May 18, 2016 (CN) .................... 2016 2 0544787 U

(51) Int. Cl.
| | | |
|---|---|---|
| H04R 25/00 | (2006.01) | |
| H04R 1/10 | (2006.01) | |
| A61B 5/024 | (2006.01) | |
| A61B 5/00 | (2006.01) | |
| H04R 23/00 | (2006.01) | |

(52) U.S. Cl.
CPC ....... *H04R 1/1016* (2013.01); *A61B 5/02438* (2013.01); *A61B 5/02444* (2013.01); *A61B 5/6803* (2013.01); *A61B 5/6817* (2013.01); *H04R 1/1066* (2013.01); *H04R 1/1091* (2013.01); *H04R 23/008* (2013.01); *H04R 25/658* (2013.01); *H04R 2225/025* (2013.01)

(58) Field of Classification Search
CPC .. H04R 1/1016; H04R 1/1066; H04R 1/1091; H04R 23/008; H04R 25/658; H04R 2225/025; H04R 2420/07; A61B 5/02444; A61B 5/6803; A61B 5/6815; A61B 5/6817; A61B 5/02438
USPC ....... 381/322, 324, 328, 330, 172, 370, 374, 381/380, 381, 382, 384; 600/300, 479, 600/485, 500
See application file for complete search history.

(56) References Cited

U.S. PATENT DOCUMENTS

| | | | |
|---|---|---|---|
| 6,283,915 B1 * | 9/2001 | Aceti .................... | A61B 5/0002 128/903 |
| 7,175,601 B2 * | 2/2007 | Verjus ................ | A61B 5/02438 600/485 |
| 2016/0199001 A1 * | 7/2016 | Lee ...................... | A61B 5/6817 600/479 |

* cited by examiner

*Primary Examiner* — Huyen D Le
(74) *Attorney, Agent, or Firm* — Lin & Associates Intellectual Property, Inc.

(57) ABSTRACT

An optical heart rate earphone includes a front housing, a circuit board assembly, a rear housing assembled to a rear end of the front housing, and a light pipe. The front housing has a sound tube. At least one portion of the sound tube forms at least one light transmission gap. The circuit board assembly includes a circuit board and at least one optical sensor. The at least one optical sensor is corresponding to the at least one light transmission gap. The light pipe has a circular base. At least one portion of a periphery of the base protrudes rearward to form at least one transmittance slice. The light pipe is assembled to the sound tube. The at least one transmittance slice is wedged in the at least one light transmission gap.

16 Claims, 4 Drawing Sheets

OPTICAL HEART RATE EARPHONE

CROSS-REFERENCE TO RELATED APPLICATION

The present application is based on, and claims priority form, China Patent Application No. 201620544787.2, filed May 18, 2016, the disclosure of which is hereby incorporated by reference herein in its entirety.

BACKGROUND OF THE INVENTION

1. Field of the Invention

The present invention generally relates to an earphone, and more particularly to an optical heart rate earphone.

2. The Related Art

When a sporter is in motion, measuring physiological signals is one of the most important needs of the sporter. The most important and valuable indexes of the physiological signals are heart rates. A function of measuring the heart rates has become a representative function of a current wearable physiological measurement device.

The current wearable physiological measurement device mainly measures electrical signals. But the current wearable physiological measurement device for measuring the electrical signals has a complex structure, and it is complex for the sporter to wear the physiological measurement device. Moreover, it has no way of supporting the sporter to measure the electrical signals at any time.

A wearable physiological measurement device for mainly measuring optical signals solves the above-mentioned problems. Currently, the wearable physiological measurement device for mainly measuring the optical signals is usually an optical heart rate earphone. The optical heart rate earphone is usually an in-ear type earphone. The optical heart rate earphone includes an optical sensor and an earphone, so the optical heart rate earphone can not only play music, but also measure optical signals to measure the heart rates. Currently, a measuring position of the optical heart rate earphone is usually at an auricle. The optical sensor is located adjacent to an inferior margin of the auricle, the measured optical signals are emitted by a surface of skin of the auricle.

However, the skin of the auricle is thinner, environmental light easily penetrates through the skin of the auricle, so the optical signals are easily interfered by the environmental light that makes the heart rates are measured inaccurately.

In view of the aforesaid description, the above-mentioned problems has become an important issue to be solved by persons skilled in the art, so an innovative optical heart rate earphone need be reasonably designed to effectively improve the above-mentioned problems.

SUMMARY OF THE INVENTION

An object of the present invention is to provide an optical heart rate earphone. The optical heart rate earphone includes a front housing, a circuit board assembly, a rear housing and a light pipe. The front housing has a case body, and a hollow barrel-shaped sound tube extended frontward from a front of the case body. At least one portion of the sound tube forms at least one light transmission gap penetrating a front edge of the sound tube. The circuit board assembly includes a fastening element, a circuit board, a loudspeaker and at least one optical sensor. A middle of the fastening element opens a tuning hole penetrating therethrough along a front-to-rear direction. The circuit board includes a fastening frame, an assembling portion, and a connecting portion connected between the fastening frame and the assembling portion. The fastening element is received in the fastening frame. The fastening element together with the fastening frame is assembled in the sound tube. The loudspeaker is assembled to the assembling portion of the circuit board and faces to the tuning hole. The at least one optical sensor is fastened to an outer surface of the fastening frame and corresponding to the at least one light transmission gap. The rear housing is assembled to a rear end of the front housing. The light pipe has a circular base. The base opens a sound hole corresponding to the tuning hole. At least one portion of a periphery of the base protrudes rearward to form at least one transmittance slice corresponding to the at least one light transmission gap. The light pipe is assembled to the sound tube. The at least one transmittance slice is wedged in the at least one light transmission gap. The light pipe and the sound tube are capable of being together inserted into an ear canal for measuring heart rates.

As described above, the at least one optical sensor of the circuit board assembly of the optical heart rate earphone is correspondingly placed at a lower portion of an ear canal, the at least one optical sensor measures optical signals of the inside of the ear canal through the at least one transmittance slice of the light pipe, so that heart rates are measured accurately. Therefore, the optical heart rate earphone is reasonably designed.

BRIEF DESCRIPTION OF THE DRAWINGS

The present invention will be apparent to those skilled in the art by reading the following description, with reference to the attached drawings, in which.

DETAILED DESCRIPTION OF THE PREFERRED EMBODIMENT

Figure 1:
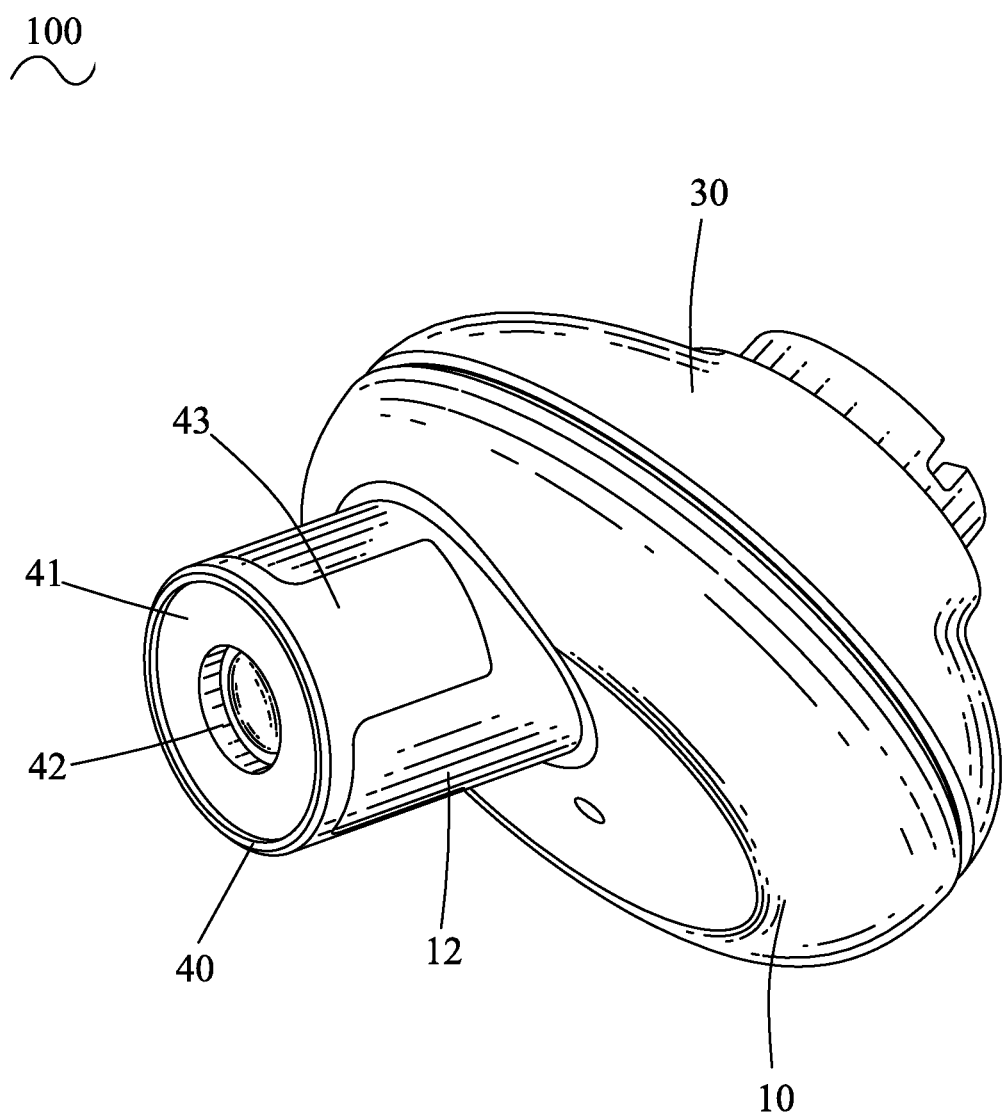
FIG. 1 is a perspective view of an optical heart rate earphone in accordance with a preferred embodiment of the present invention.

With reference to FIG. 1 to FIG. 4, an optical heart rate earphone 100 in accordance with a preferred embodiment of the present invention is shown. The optical heart rate earphone 100 includes a front housing 10, a circuit board assembly 20, a rear housing 30 and a light pipe 40. In this preferred embodiment, the optical heart rate earphone 100 is an in-ear type earphone.

Figure 2:
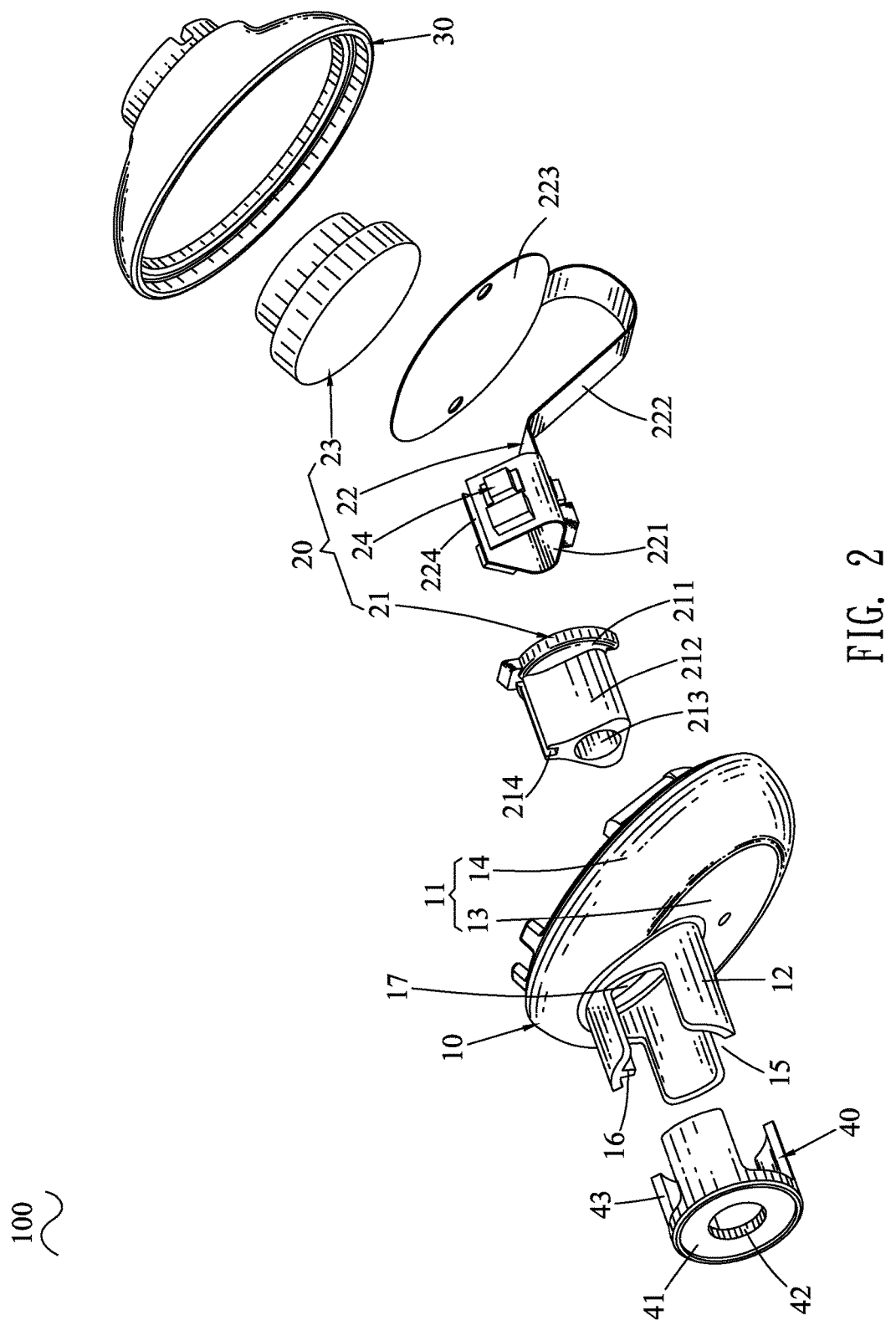
FIG. 2 is an exploded view of the optical heart rate earphone of FIG. 1.

Referring to FIG. 2, the front housing 10 has a case body 11, and a hollow barrel-shaped sound tube 12 extended frontward from a front of the case body 11. The case body 11 has a disc-shaped sealing cover 13, and a ring-shaped sealing barrel 14 arched outward and rearward from an outer periphery of the sealing cover 13. Specifically, a junction between the sealing cover 13 and the sealing barrel 14 opens a through-hole 17 penetrating therethrough. A periphery wall of the through-hole 17 protrudes frontward to form the hollow barrel-shaped sound tube 12. So the through-hole 17 is communicated with an inside room of the sound tube 12. At least one portion of the sound tube 12 forms at least one light transmission gap 15 penetrating a front edge of the sound tube 12. Specifically, the sound tube 12 forms three light transmission gaps 15 penetrating the front edge of the sound tube 12. A portion of an inner surface of the sound tube 12 protrudes inward to form a buckling portion 16 extending along a front-to-rear direction. The buckling portion 16 is of a strip shape.

Referring to FIG. 2, the circuit board assembly 20 includes a fastening element 21, a circuit board 22, a loudspeaker 23 and at least one optical sensor 24. In this preferred embodiment, the at least one optical sensor 24 is an LED sensor.

Figure 3:
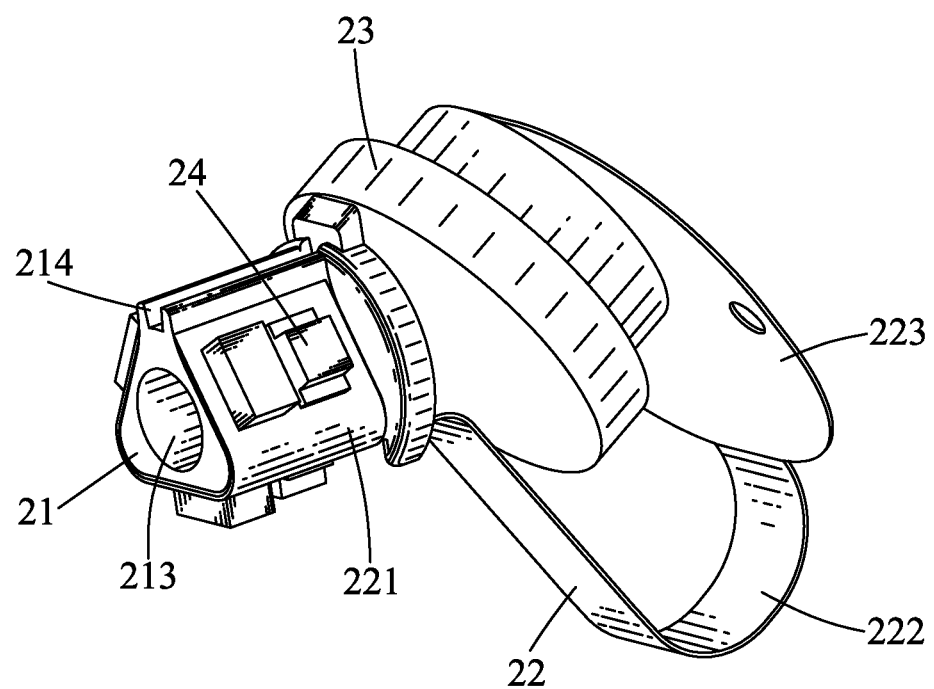
FIG. 3 is a perspective view of a circuit board assembly of the optical heart rate earphone of FIG. 1.
Figure 4:
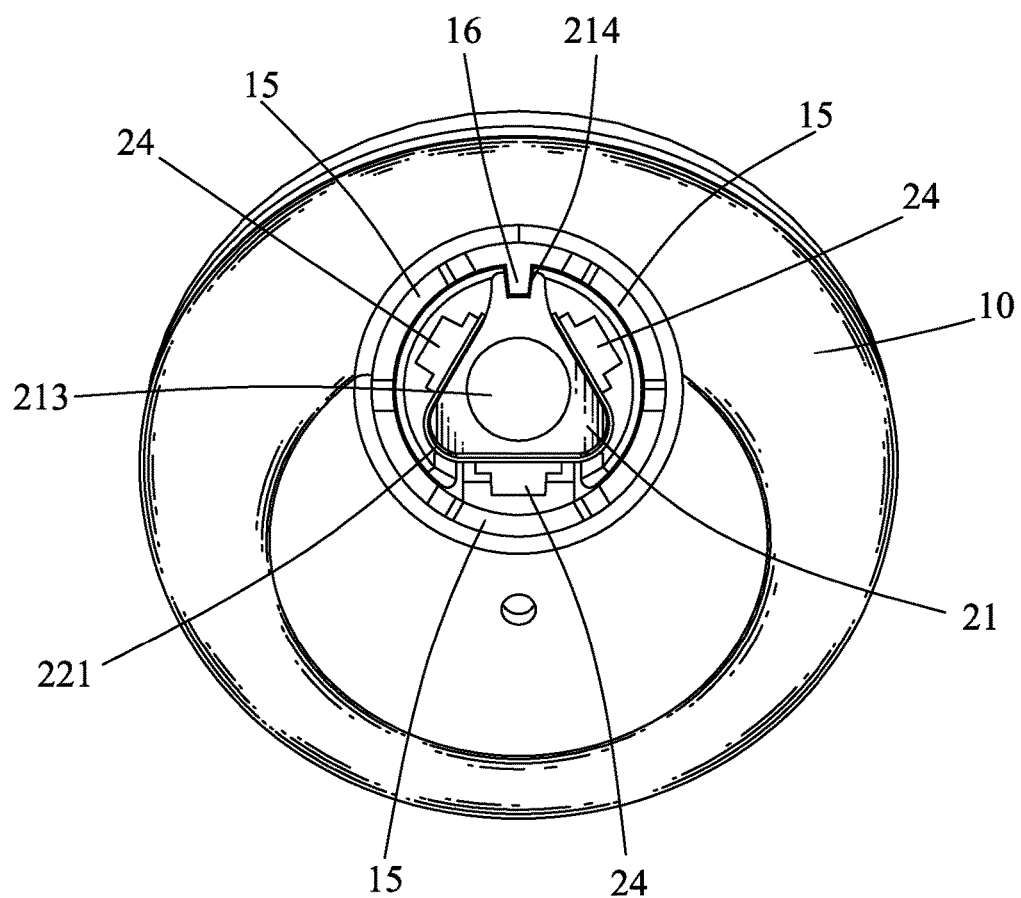
FIG. 4 is a schematic diagram of the optical heart rate earphone of FIG. 1, wherein a light pipe is omitted.

Referring to FIG. 2 to FIG. 4, a middle of the fastening element 21 opens a tuning hole 213 penetrating therethrough along the front-to-rear direction. The fastening element 21 has a limiting portion 211, and a fastening portion 212 protruded frontward from a front of the limiting portion 211. The fastening portion 212 is of an approximately triangular prism shape. The fastening portion 212 has a substantially triangular front surface and a substantially triangular rear surface. A portion of the fastening portion 212 is recessed inward to form a buckling slot 214 extending along the front-to-rear direction. The buckling slot 214 penetrates through the front surface and the rear surface of the fastening portion 212. The buckling slot 214 is matched with the buckling portion 16. In this preferred embodiment, one arris of the fastening portion 212 is recessed inward to form the buckling slot 214 extending along the front-to-rear direction.

The circuit board 22 includes a fastening frame 221, an assembling portion 223, and a connecting portion 222 connected between the fastening frame 221 and the assembling portion 223. The fastening frame 221 is of an approximately hollow triangular prism shape and is matched with the fastening portion 212 of the fastening element 21. A portion of the fastening frame 221 is opened freely to form an opening 224 extending along the front-to-rear direction and penetrating through a front and a rear thereof. The fastening element 21 is received in the fastening frame 221. The fastening portion 212 is fastened in the fastening frame 221. The opening 224 is corresponding to the buckling slot 214. The loudspeaker 23 is assembled to the assembling portion 223 of the circuit board 22 and faces to the tuning hole 213 of the fastening element 21.

The at least one optical sensor 24 is fastened to an outer surface of the fastening frame 221 of the circuit board 22 and corresponding to the at least one light transmission gap 15 of the front housing 10. The at least one optical sensor 24 is fastened to a periphery of the fastening frame 221. In this preferred embodiment, the circuit board assembly 20 includes three optical sensors 24 fastened to the periphery of the fastening frame 221. Specifically, the three optical sensors 24 are fastened to three outer surfaces of the fastening frame 221 and separately corresponding to the three light transmission gaps 15.

The circuit board assembly 20 is assembled in the front housing 10. The fastening element 21 together with the fastening frame 221 is assembled in the sound tube 12. The buckling portion 16 is buckled in the buckling slot 214. The at least one optical sensor 24 is correspondingly assembled to the at least one light transmission gap 15.

The rear housing 30 is assembled to a rear end of the front housing 10. So the circuit board assembly 20 is surrounded between the rear housing 30 and the front housing 10.

Referring to FIG. 1 and FIG. 2, the light pipe 40 has a circular base 41. A diameter of the base 41 is consistent with a diameter of the sound tube 12 of the front housing 10. The base 41 opens a sound hole 42. At least one portion of a periphery of the base 41 protrudes rearward to form at least one transmittance slice 43. The light pipe 40 is assembled to the sound tube 12. The at least one transmittance slice 43 is corresponding to the at least one light transmission gap 15. The at least one transmittance slice 43 is wedged in the at least one light transmission gap 15. A rear wall of the at least one light transmission gap 15 abuts against a rear of the light pipe 40. The sound hole 42 is communicated with the inside room of the sound tube 12. The sound hole 42 is corresponding to the tuning hole 213 of the fastening element 21 of the circuit board assembly 20. In this preferred embodiment, three portions of the periphery of the base 41 protrude rearward to form three transmittance slices 43. The three transmittance slices 43 are separately wedged in the three light transmission gaps 15.

The light pipe 40 and the sound tube 12 are capable of being together inserted into an ear canal for measuring heart rates. When the optical heart rate earphone 100 is in use, the light pipe 40 and the sound tube 12 of the front housing 10 are inserted into the ear canal. The at least one optical sensor 24 is correspondingly placed at a lower portion of an inside of the ear canal. The heart rates are measured more accurately by virtue of the at least one optical sensor 24 measuring optical signals of the inside of the ear canal through the at least one transmittance slice 43 of the light pipe 40. Specifically, the three optical sensors 24 are placed at the lower portion of the inside of the ear canal. The heart rates are measured more accurately by virtue of the optical sensors 24 measuring optical signals of the lower portion of the inside of the ear canal.

In this preferred embodiment, the circuit board assembly 20 further includes a Bluetooth module (not shown). A user is capable of answering a telephone or enjoying music by means of the Bluetooth module being able to transmit the optical signals sensed by the at least one optical sensor 24 to a peripheral equipment for a real-time measurement and being able to transmit signals from the peripheral equipment to the user.

As described above, the at least one optical sensor 24 of the circuit board assembly 20 of the optical heart rate earphone 100 is correspondingly placed at the lower portion of the ear canal, the at least one optical sensor 24 measures the optical signals of the inside of the ear canal through the at least one transmittance slice 43 of the light pipe 40, so that the heart rates are measured more accurately. Therefore, the optical heart rate earphone 100 is reasonably designed.

What is claimed is:
1. An optical heart rate earphone, comprising:
a front housing having a case body, and a hollow barrel-shaped sound tube extended frontward from a front of the case body, at least one portion of the sound tube forming at least one light transmission gap penetrating a front edge of the sound tube;
a circuit board assembly including a fastening element, a circuit board, a loudspeaker and at least one optical sensor, a middle of the fastening element opening a tuning hole penetrating therethrough along a front-to-rear direction, the circuit board including a fastening frame, an assembling portion, and a connecting portion connected between the fastening frame and the assembling portion, the fastening element being received in the fastening frame, the fastening element together with the fastening frame being assembled in the sound tube, the loudspeaker being assembled to the assembling portion of the circuit board and facing to the tuning hole, the at least one optical sensor being fastened to an outer surface of the fastening frame and corresponding to the at least one light transmission gap;

a rear housing assembled to a rear end of the front housing; and a light pipe having a circular base, the base opening a sound hole corresponding to the tuning hole, at least one portion of a periphery of the base protruding rearward to form at least one transmittance slice corresponding to the at least one light transmission gap, the light pipe being assembled to the sound tube, the at least one transmittance slice being wedged in the at least one light transmission gap;

wherein the light pipe and the sound tube are capable of being together inserted into an ear canal for measuring heart rates.

2. The optical heart rate earphone as claimed in claim 1, wherein a portion of an inner surface of the sound tube protrudes inward to form a buckling portion extending along a front-to-rear direction, the fastening element has a limiting portion, and a fastening portion protruded frontward from a front of the limiting portion, a portion of the fastening portion is recessed inward to form a buckling slot extending along the front-to-rear direction, the buckling portion is buckled in the buckling slot.

3. The optical heart rate earphone as claimed in claim 2, wherein a portion of the fastening frame is opened freely to form an opening extending along the front-to-rear direction and penetrating through a front and a rear thereof, the fastening element is received in the fastening frame, the opening is corresponding to the buckling slot.

4. The optical heart rate earphone as claimed in claim 2, wherein the buckling slot penetrates through a front surface and a rear surface of the fastening portion.

5. The optical heart rate earphone as claimed in claim 2, wherein the fastening portion is of an approximately triangular prism shape, the fastening frame is of an approximately hollow triangular prism shape and matched with the fastening portion, the fastening portion is fastened in the fastening frame.

6. The optical heart rate earphone as claimed in claim 5, wherein one arris of the fastening portion is recessed inward to form the buckling slot extending along the front-to-rear direction.

7. The optical heart rate earphone as claimed in claim 1, wherein a diameter of the base is consistent with a diameter of the sound tube of the front housing.

8. The optical heart rate earphone as claimed in claim 1, wherein a rear wall of the at least one light transmission gap abuts against a rear of the light pipe.

9. The optical heart rate earphone as claimed in claim 1, wherein the optical heart rate earphone is an in-ear type earphone.

10. The optical heart rate earphone as claimed in claim 1, wherein the case body has a disc-shaped sealing cover, and a ring-shaped sealing barrel arched outward and rearward from an outer periphery of the sealing cover, a junction between the sealing cover and the sealing barrel opens a through-hole penetrating therethrough, a periphery wall of the through-hole protrudes frontward to form the sound tube, the through-hole is communicated with an inside room of the sound tube.

11. The optical heart rate earphone as claimed in claim 1, wherein the at least one optical sensor is an LED sensor.

12. The optical heart rate earphone as claimed in claim 1, wherein the at least one optical sensor is fastened to a periphery of the fastening frame.

13. The optical heart rate earphone as claimed in claim 1, wherein the at least one optical sensor is correspondingly placed at a lower portion of an inside of the ear canal.

14. The optical heart rate earphone as claimed in claim 1, wherein the circuit board assembly includes three optical sensors fastened to a periphery of the fastening frame, the three optical sensors are placed at a lower portion of an inside of the ear canal.

15. The optical heart rate earphone as claimed in claim 14, wherein the sound tube forms three light transmission gaps penetrating the front edge of the sound tube, the fastening frame is of an approximately hollow triangular prism shape, the three optical sensors are fastened to three outer surfaces of the fastening frame and separately corresponding to the three transmission gaps.

16. The optical heart rate earphone as claimed in claim 15, wherein three portions of a periphery of the base protrude rearward to form three transmittance slices, the three transmittance slices are separately wedged in the three light transmission gaps.

* * * * *